(12) United States Patent
Lee et al.

(10) Patent No.: US 7,975,532 B2
(45) Date of Patent: Jul. 12, 2011

(54) TRANSPORTABLE APPARATUS AND METHOD FOR ENABLING DETERMINATION OF ERODIBILITY CHARACTERISTICS

(75) Inventors: Landris T. Lee, Vicksburg, MS (US); Perry A. Taylor, Raymond, MS (US); Johannes L. Wibowo, Vicksburg, MS (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 423 days.

(21) Appl. No.: 12/267,138

(22) Filed: Nov. 7, 2008

(65) Prior Publication Data

US 2010/0116037 A1    May 13, 2010

(51) Int. Cl.
*G01N 17/00* (2006.01)
(52) U.S. Cl. .......................................................... 73/86
(58) Field of Classification Search ................... 73/86
See application file for complete search history.

(56) References Cited

U.S. PATENT DOCUMENTS

| | | | | |
|---|---|---|---|---|
| 2,923,148 | A * | 2/1960 | Kirkham et al. | 73/86 |
| 5,243,850 | A * | 9/1993 | Hanson | 73/86 |
| 5,331,847 | A * | 7/1994 | Hanson | 73/86 |
| 6,260,409 | B1 * | 7/2001 | Briaud et al. | 73/86 |
| 6,494,084 | B1 * | 12/2002 | Roberts et al. | 73/86 |
| 6,679,105 | B1 * | 1/2004 | Jepsen et al. | 73/86 |

* cited by examiner

*Primary Examiner* — Hezron Williams
*Assistant Examiner* — Nathaniel Kolb
(74) *Attorney, Agent, or Firm* — Earl H. Baugher, Jr.

(57) ABSTRACT

A transportable system and method for determining erodibility of a surface such as that of an earthen embankment. Select embodiments deploy an instrumented portable bottomless open channel test enclosure, either a manifold or an inlet to a flume, and sufficient piping and valves to provide a fluid flow over a surface of interest. Select embodiments use mounts, such as spikes, affixed to the bottom edges of the open channel to position the channel flush against the surface, thus reducing or preventing fluid leakage along the periphery. Select embodiments emulate a hydraulic open channel having smooth vertical sides as may be found in a civil engineering laboratory. Select embodiments incorporate an external pump, gauges for taking measurements while fluid flows through the channel, an inlet and an outlet and a re-cycling sub-system from the outlet to the inlet.

21 Claims, 2 Drawing Sheets

TRANSPORTABLE APPARATUS AND METHOD FOR ENABLING DETERMINATION OF ERODIBILITY CHARACTERISTICS

STATEMENT OF GOVERNMENT INTEREST

Under paragraph 1(a) of Executive Order 10096, the conditions under which this invention was made entitle the Government of the United States, as represented by the Secretary of the Army, to an undivided interest therein on any patent granted thereon by the United States. This and related patents are available for licensing to qualified licensees. Please contact Phillip Stewart at 601 634-4113.

BACKGROUND

Dams and levees are subject to erosion caused by steady-state and transient-state hydraulic loads exceeding critical velocities and critical shear stresses. Appropriate test methods have not been available to measure erodibility indices, such as erosion rate, critical shear stress, water overtopping critical velocity, water over-washing cyclical critical velocity, surface roughness, and threshold resistance to erosion initiation.

Conventional testing devices, such as laboratory flumes or on-site field flumes and the like, require samples of soil to be extracted from the surface and physically placed in an erosion testing device. The soil structure and shear strength properties are inadvertently altered, even if utmost attention is given to retrieving an "undisturbed" sample. If vegetative cover is to be tested in addition to the soil surface, either the vegetation must be artificially grown in a flume or the soil and root structure is significantly disturbed during sample retrieval and preparation. Existing laboratory or field testing devices are unable to address disparities between as-tested samples and in-situ samples.

Field plots for erosion testing, typically used in agronomy research, provide more accurate erodibility indices and hydraulic indices since this type of field testing is conducted in-situ. However, field plots are unable to vary overflow flow rate, velocity, or depth. Their purpose is to research inter-rill and rill erosion caused by rainfall intensity and runoff parameters. Field plots are not man-portable or transportable.

Select embodiments of the present invention enable on-site erodibility testing on surfaces having a wide variety of textures, from bare soil surfaces, to graminaceous or herbaceous vegetated surfaces often found on dams and levees, to geosynthetic turf reinforcement mat overlays. Select embodiments of the present invention facilitate erosion testing beyond conventional tests on bare soil surfaces. Select embodiments of the present invention may be employed on bare soil, fissured soil, root clumps, and other real-life heterogeneous surface conditions. Select embodiments of the present invention replicate laboratory hydraulic flume experiments, correlating laboratory results to in-situ test results.

Select embodiments of the present invention provide variable hydraulic loads on a test plot while addressing compatibility issues arising from off-site versus on-site test results by controlling on-site hydraulic loading parameters much as is done in a laboratory. Further, there are no sampling compatibility issues because a sampled plot is a test plot enclosed within the test configuration.

Further, select embodiments of the present invention may be employed to test dam and levee armoring products such as turf reinforcement mats by placing on a mat similar to the way employed on natural soil.

DETAILED DESCRIPTION

Figure 1:
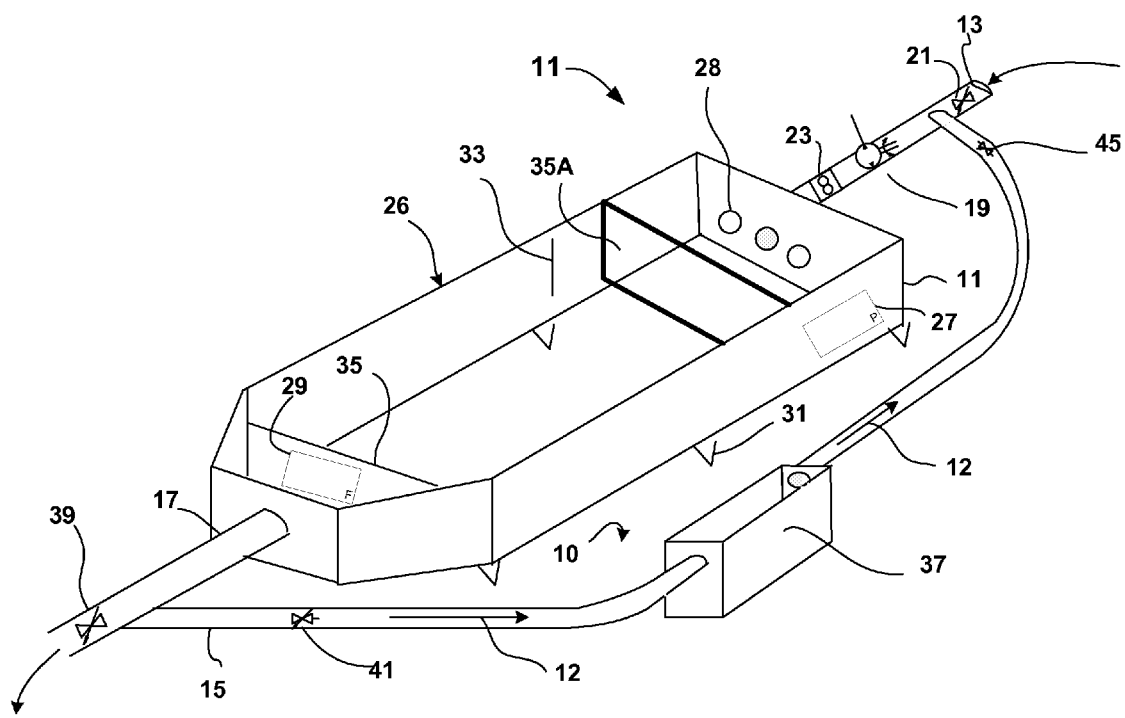
FIG. 1 is a schematic illustration of a first alternative embodiment of the present invention.

Select embodiments of the present invention provide a transportable apparatus and method for on-site testing to assess erodibility without physically removing or relocating soil and vegetation. Select embodiments of the present invention physically simulate the erosive forces and hydraulic loads imposed on earthen embankments during storm surge, flood, or overtopping events.

In select embodiments of the present invention, the apparatus comprises a configuration having an open top and at least a partially open bottom, and means for mounting the configuration flush against either a level or sloped embankment test section so that the edges of the configuration enclose the test section and prevent water leakage. Thus, the apparatus emulates a hydraulic open channel having smooth vertical sides, such as may be employed in a laboratory. In select embodiments of the present invention, the apparatus incorporates a water inlet from an external pump, instruments for taking at least hydraulic and erosion measurements, and a water outlet.

In select embodiments of the present invention, a method of testing erodibility in situ is provided. The method comprises: providing a transportable configuration having an open top and at least a partially open bottom, mounting the configuration flush against a level or sloped embankment test section so that the edges of the configuration enclose the test section and prevent water leakage, inputting water to the configuration from an external pump, taking hydraulic and erosion measurements, and outputting water from the configuration.

Select embodiments of the present invention provide a transportable apparatus and method for taking physical measurements of the erodibility of earthen embankments. The apparatus allows testing to be conducted on the intact surface of the earthen embankment by controlling the hydraulic loading that initiates and propagates soil erosion. Water flow over the embankment's vegetated cover or bare soil surface, enclosed by a configuration having an open top and bottom and enclosed sides, initiates erosion and subsequent progress. Instruments collect water measurement data for calculating such characteristics as the vegetated or bare surface friction loss, hydraulic shear stress, critical hydraulic velocity, critical shear stress, erosion rate, erodibility index (coefficient of erodibility) values, and the like.

Select embodiments of the present invention employ a transportable system for measuring erodibility comprising a configuration having a length, a width and a depth, an open top and a partially-open bottom, two sides defining the length and the depth and having top and bottom edges, two ends defining the width and depth and having top and bottom edges, one or more inlets and one or more outlets, such that the inlet and outlet facilitate movement of a fluid; mounts to affix the configuration approximately flush against a surface so that bottom edges defining the periphery of the configuration enclose a section of the surface and reduce or eliminate fluid leaks along the periphery, such that the configuration emulates a hydraulic open channel having smooth vertical sides as may be employed in a research laboratory; a source of fluid; a pump in operable communication with the source of fluid and the configuration, such that the pump at least provides fluid from the source to the configuration; one or more instruments for at least collecting data while fluid flows through the configuration, such that the fluid exits the system at the outlet to permit the instruments to collect data.

Select embodiments of the present invention employ spikes as said mounts. Select embodiments of the present invention disposed spikes on one or more of the bottom edges.

Select embodiments of the present invention use sheet aluminum at least in part for the configuration. Select embodiments of the present invention employ extruded acrylic sheet at least in part for the configuration.

Select embodiments of the present invention employ one or more baffles in the configuration. Select embodiments of the present invention incorporate one or more weirs in the configuration.

Select embodiments of the present invention incorporate matched pairs of vertical slots in the sides of the configuration, a first of each pair arranged on one side at the same length along the configuration as a second of the pair on the other side, such that each of the pairs of slots facilitates the fitting of one baffle.

Select embodiments of the present invention incorporate one or more baffles, each baffle disposed in one of a pair of vertical slots.

Select embodiments of the present invention incorporate one or more weirs, each weir disposed in a pair of vertical slots.

Select embodiments of the present invention incorporate a flume comprising an inlet orifice, two sides, an open top, and a non-open bottom such that the fluid entering the configuration becomes evenly distributed along the width of the configuration.

Select embodiments of the present invention incorporate a manifold at the inlet to evenly distribute fluid across the width of the test area.

Select embodiments of the present invention employ one or more gauges as instruments. Select embodiments of the present invention employ gauges selected from the group consisting of pressure gauges, flow rate gauges, velocity gauges, depth gauges, and combinations thereof.

Select embodiments of the present invention employ a recirculation system. In select embodiments of the present invention the recirculation system comprises one or more sub-systems connected to the inlet and outlet for re-cycling at least part of the fluid exiting the system, a sub-system further comprising: one or more valves for controlling re-cycling and one or more settling tanks.

In select embodiments of the present invention a system for determining erodibility (erosion potential) of an earthen surface of an embankment due to at least liquid abrasion comprises: a configuration having a length, a width and a depth, an open top and a partially-open bottom, two sides defining the length and depth and having top and bottom edges; two ends defining the width and depth and having top and bottom edges, and having one or more inlets and one or more outlets, such that the inlet and outlet facilitates movement of the liquid; mounts to affix the configuration approximately flush against the earthen surface so that bottom edges defining the periphery of the configuration enclose a section of the earthen surface and at least reduce leaks of the liquid along the periphery, such that the configuration emulates a hydraulic open channel having smooth vertical sides as may be employed in a research laboratory; a source of liquid; a pump for transferring the liquid from its source, the pump at least providing the liquid to the configuration from the source; one or more instruments for collecting data while the liquid flows through the configuration.

In select embodiments of the present invention a method of testing the erodibility of an earthen embankment surface comprises: providing a configuration having a length, a width and a depth, an open top and a partially-open bottom; two sides defining the length and the depth and having top and bottom edges; two ends defining the width and the depth and having top and bottom edges; one or more inlets and one or more outlets, the inlet and outlet facilitating movement of a fluid; providing mounts to affix the configuration approximately flush against the surface so that bottom edges defining the periphery of the configuration enclose a section of the surface and at least reduce fluid leaks along the periphery, such that the configuration emulates a hydraulic open channel having smooth vertical sides as may be employed in a research laboratory; mounting the configuration over the earthen surface by inserting the mounts into the earthen surface: providing a source of fluid; providing a pump to transfer fluid from the source of fluid to the configuration, pumping the fluid to the inlet from the source; providing one or more instruments; and collecting data with the instruments while the fluid flows through the configuration.

In select embodiments of the present invention the method further comprises recycling the fluid.

In select embodiments of the present invention the method further comprises releasing the fluid.

In select embodiments of the present invention spikes disposed on the bottom edge are pressed into the soil to affix the configuration to the earthen surface.

Refer to FIG. 1. In select embodiments of the present invention, water is supplied to a configuration 11 from either an external source 13 or from a flow recirculation conduit 15 connected to an outflow connector 17. In select embodiments of the present invention, water is pumped to a configuration 11 using a pump 19 with a shut-off valve 21 and a pressure or flow rate gage 23. In select embodiments of the present invention, water enters a manifold 28 to evenly distribute flow into the open-bottomed test enclosure 26 of configuration 11. In select embodiments of the present invention, flow measurements to establish erosion parameters are taken using gages 23, 27, and 29.

Figure 2:
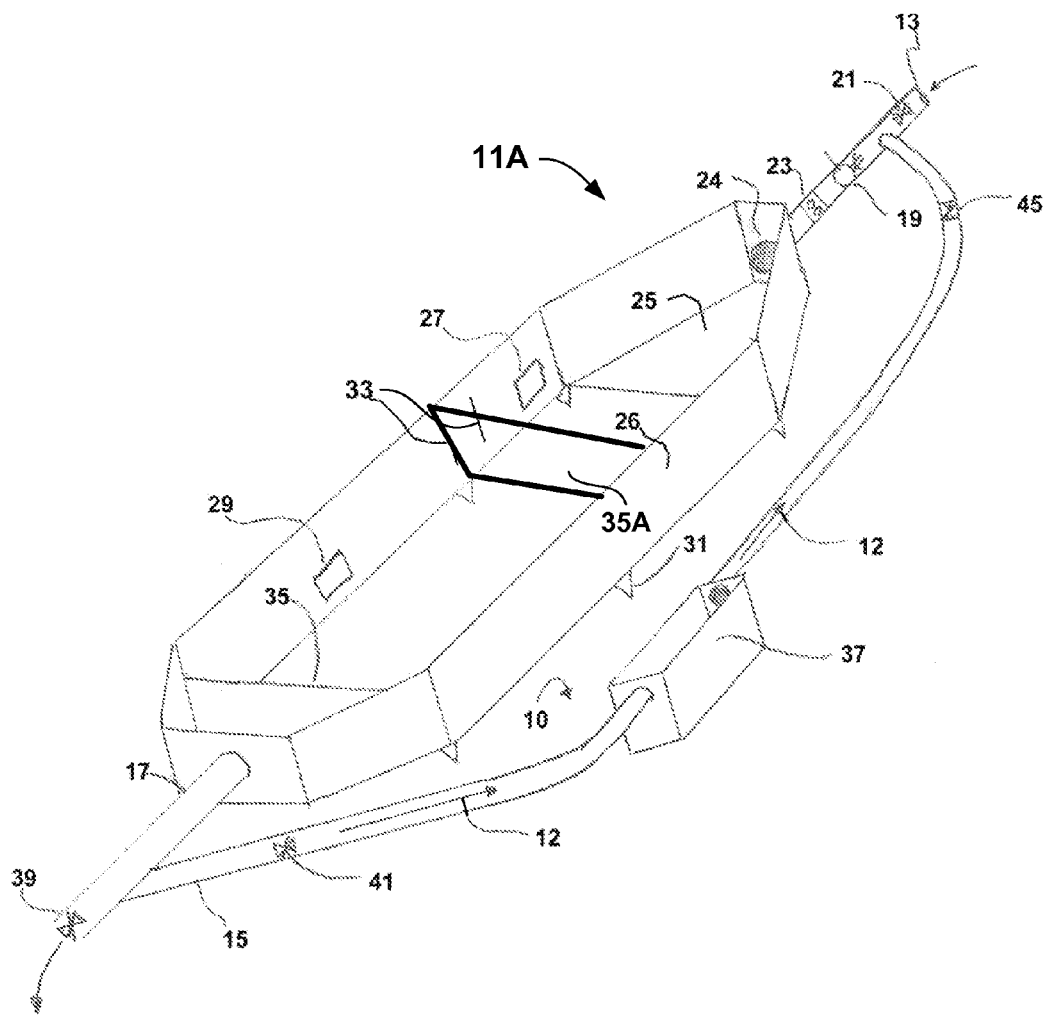
FIG. 2 is a schematic illustration of a second alternative embodiment of the present invention.

Refer to FIG. 2, an alternative embodiment of the present invention, employing a single inlet 24 instead of a manifold 28 in configuration 11A. In select embodiments of the present invention, water enters a flume 25 from the single inlet 24 to evenly distribute flow into the open-bottomed test enclosure 26 of the configuration 11A. In select embodiments of the present invention, flow measurements to establish erosion parameters are taken using gages 23, 27, and 29.

In select embodiments of the present invention, the configurations 11, 11A comprise a man-portable rigid frame, such as made be constructed of lightweight aluminum or extruded acrylic sheet [Poly(methyl methacrylate) (PMMA) or poly(methyl 2-methylpropenoate)], marketed as Plexiglas, consisting of a manifold 28 or a single inlet 24 and flume 25, both configurations 11, 11A having an open top and non-open bottom, and a test enclosure 26 having an open top and open bottom, and spikes 31 along the perimeter of the bottom edge of the configurations 11, 11A. The configuration 11 is mounted flush to the test plot, e.g., an earthen embankment, by manually embedding the spikes 31 into the soil 10. The edges of the configuration 11 enclose the surface 10 to prevent leakage at the periphery of the configuration 11. When positioned properly onto the surface 10, the test enclosure 26 acts as a hydraulic open channel having smooth vertical sides.

Selectable commercial off-the-shelf test gages 23, 27, and 29, allow measurement of hydraulic parameters required for evaluating surface erodibility.

Select embodiments of the present invention permit quantification of the differential velocity (velocity head gradient) across the vegetated or bare soil levee surface which in turn allows calculation of friction loss (i.e. surface roughness or drag coefficient), Froude number, and Manning's friction factor "n". Once "n" is known, the effective shear stress at the soil-water interface is calculated. Adjusting flow rate and velocity allows calculation of the permissible tractive force (critical hydraulic shear stress) prior to actual removal of soil surface particles. Further increasing the flow rate initiates surface erosion and the actual erosion rate (amount of soil particles removed over time) may be observed and documented. Finally, knowing the effective shear stress, critical shear stress, and erosion rate allows calculation of the erodibility coefficient of a sloped levee surface. Select embodiments of the present invention for testing levee sites with grasses and weeds, for example, have approximate dimensions of up to about 8 ft in length, up to about 3 ft in width, and about 2 ft in depth (height)

In select embodiments of the present invention, test gages 23 comprise commercial off-the-shelf (COTS) water flow rate measurement devices to monitor the flow rate of the pump 19, or alternatively comprise a COTS water pressure measurement device to monitor outlet pressure of the pump 19. In select embodiments of the present invention, test gages 27 and 29 comprise COTS water velocity measurement devices that allow real time monitoring and recordable data collection of water velocity. In select embodiments of the present invention, recordable data collected from test gages 27 and 29 enable post-test calculations of water discharge-area-velocity parameters required for evaluating erodibility. Test gages 27 and 29 are fixably positioned on the test enclosure 26 or detachable from the test enclosure 26 to take water velocity measurements at locations within the enclosed periphery of the test enclosure 26. In select embodiments of the present invention, there may be disposed vertical slots 33 along the length of the interior of the configuration 11, enabling placement of baffles 35A and weirs 35. Selective weir placement enables calibration or duplication of water measurement data collected from gages 23, 27, and 29. Selective baffle 35A placement and removal enables time-varying water inflow or cyclical water velocity distribution useful for evaluating dynamic (transient-state) erodibility.

In select embodiments of the present invention, the inlet (normally upper) end of the configuration 11 allows water from a pump 19 to enter the configuration 11 with an inflow distribution pattern established by either a manifold 28 or a single inlet 24 and flume 25. In select embodiments of the present invention, inflow water pressure, flow rate, and the like are monitored using pressure gages, flow rate gages, velocity gages and the like 23, 27, and 29, preferably COTS items, to maintain a consistent inflow rate through either a manifold 28 or the inlet orifice 24, to establish a uniformly distributed flow pattern through the flume 25, and to perform water flow measurements along the width and length of the test enclosure 26.

In select embodiments of the present invention, the discharge (normally lower) end of the test enclosure 26 comprising configuration 11 incorporates one or more interchangeable interior baffles 35A or weirs 35 to provide a means to collect water measurements, and a pipe outflow connector 17. In select embodiments of the present invention, the outflow connector 17 allows water to discharged, be recycled via a flow recirculation conduit 15 into a recycling tank 37, or both. This allows measurement of eroded sediment quantity, effluent quality, and the like. Shut off valves 39 and 41 allow flow discharge options for bypass or recirculation. In select embodiments of the present invention, water from the recycling tank 37 flows into the inflow 13. Shutoff valve 21 provides for water discharge and bypass.

In select embodiments of the present invention, input water flow is controllable by a pump 19 to allow either steady-state or transient-state flow regimes. Hydraulic measurements of pressure, velocity, flow rate, and energy loss profiles, may be conducted using appropriate gages 23, 27, and 29, and interchangeable baffles 35A and weirs 35. Determination of water height, hydraulic jump, and weir overflow may also be conducted visually. Eroded sediment measurements to determine soil loss may be conducted. Erosion rates and eroded depth profiles may also be measured.

The abstract of the disclosure is provided to comply with the rules requiring an abstract that will allow a searcher to quickly ascertain the subject matter of the technical disclosure of any patent issued from this disclosure. (37 CFR §1.72 (b)). Any advantages and benefits described may not apply to all embodiments of the invention.

While the invention has been described in terms of some of its embodiments, those skilled in the art will recognize that the invention can be practiced with modifications within the spirit and scope of the appended claims. For example, although the system is described in specific examples for monitoring earthen structures, in particular levees and dams, it may be used for any type of remote monitoring and thus may be useful in such diverse applications as landslide and avalanche warning, bridge and overpass structural monitoring, mining, drilling, remediating, environmental intervention, military operations and the like. Structures monitored may be of any type ranging from naturally occurring to large manmade monoliths. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Thus, it is intended that all matter contained in the foregoing description or shown in the accompanying drawings shall be interpreted as illustrative rather than limiting, and the invention should be defined only in accordance with the following claims and their equivalents.

We claim:

1. A transportable system for in situ measuring of erodibility comprising:

a configuration having a length, a width and a depth, an open top and an at least partially-open bottom, at least two sides defining said length and said depth and having top and bottom edges, two ends defining said width and said depth and having top and bottom edges, at least one inlet located on one of said ends and at least one outlet located on the other of said ends, wherein said at least one inlet and said at least one outlet at least facilitate movement of a fluid;

mounts to affix said configuration approximately flush against a surface so that bottom edges defining the periphery of said configuration enclose a section of said surface and at least reduce fluid leaks along said periphery, wherein said configuration emulates a hydraulic open channel having smooth vertical sides such as may be employed in a research laboratory;

a source of fluid;

a pump in operable communication with said source of said fluid and said configuration, wherein said pump at least provides said fluid from said source to said configuration;

at least one instrument for at least collecting data while said fluid flows through said configuration, wherein said fluid exits said system at said outlet to permit said instruments to collect said data.

2. The system of claim 1 wherein said mounts are spikes.

3. The system of claim 2 wherein said spikes are disposed on at least one said bottom edge.

4. The system of claim 1 in which said configuration comprises at least in part sheet aluminum.

5. The system of claim 1 in which said configuration comprises at least in part extruded acrylic sheet.

6. The system of claim 1 in which said configuration incorporates at least one baffle.

7. The system of claim 1 in which said configuration incorporates at least one weir.

8. The system of claim 1 in which said configuration incorporates matched pairs of vertical slots in at least said sides, a first of said pair arranged on one said first side at the same length along said configuration as a second of said pair on said second side, wherein said pairs of slots facilitate the fitting of at least said at least one baffle.

9. The system of claim 8 incorporating at least one said baffle, each said at least one baffle disposed in one said pair of vertical slots.

10. The system of claim 8 incorporating at least one said weir, each said at least one weir disposed in one said pair of vertical slots.

11. The system of claim 1 in which said inlet incorporates at least one flume to evenly distribute said fluid along the width of said configuration.

12. The system of claim 1 in which said inlet incorporates at least one manifold to evenly distribute said fluid along the width of said configuration.

13. The system of claim 1 in which said instruments comprise at least one gauge.

14. The system of claim 13 in which the gauge is selected from the group consisting of pressure gauges, flow rate gauges, velocity gauges, depth gauges, and combinations thereof.

15. The system of claim 1 said configuration further comprising a recirculation system.

16. The system of claim 15 said recirculation system comprising:

at least one sub-system in operable communication with at least said inlet and said outlet for re-cycling at least part of said fluid exiting said system, said sub-system further comprising:

at least one valve for controlling said re-cycling; and at least one settling tank.

17. A transportable system for determining erodibility of an earthen surface of an embankment due to at least liquid abrasion comprising:

a configuration having a length, a width and a depth, an open top and an open bottom, at least two sides defining said length and said depth and having top and bottom edges, two ends defining said width and said depth and having top and bottom edges, and having at least one inlet located on one of said ends and at least one outlet located on the other of said ends, wherein said at least one inlet and said at least one outlet at least facilitate movement of liquid;

mounts to affix said configuration approximately flush against said earthen surface so that bottom edges defining the periphery of said configuration enclose a section of said earthen surface and at least reduce leaks of said liquid along said periphery, wherein said configuration emulates a hydraulic open channel having smooth vertical sides such as may be employed in a research laboratory;

a source of liquid;

a pump in operable communication with said source of said liquid and said configuration, wherein said pump at least provides said liquid to said configuration;

at least one instrument for at least collecting data while said liquid flows through said configuration.

18. A method of testing the erodibility of an earthen embankment surface comprising:

providing a transportable configuration having a length, a width and a depth, an open top and a partially open bottom, at least two sides defining said length and said depth and having top and bottom edges, two ends defining said width and said depth and having top and bottom edges, at least one inlet located on one of said ends and at least one outlet located on the other of said ends, wherein said at least one inlet and said at least one outlet at least facilitate movement of a fluid;

providing mounts to affix said configuration approximately flush against a surface so that bottom edges defining the periphery of said configuration enclose a section of said surface and at least reduce fluid leaks along said periphery, wherein said configuration emulates a hydraulic open channel having smooth vertical sides such as may be employed in a research laboratory;

mounting said configuration over said earthen surface by inserting said mounts into said earthen surface:

providing a source of fluid;

providing a pump in operable communication with said source of said fluid and said configuration, wherein said pump at least provides said fluid from said source to said configuration;

pumping said fluid to said inlet from at least said source;

providing at least one instrument; and collecting data with said at least one instrument while said fluid flows through said configuration.

19. The method of claim 18 further comprising recycling said fluid.

20. The method of claim 18 further comprising releasing said fluid.

21. The method of claim 18 said mounting comprising pressing said mounts into said earthen surface.

* * * * *